United States Patent [19]

Lucas

[11] 4,384,579
[45] May 24, 1983

[54] HYPODERMIC SYRINGE

[76] Inventor: Dieter Lucas, Schlossstrasse 5, D-7763 Öhningen-Kattenhorn, Fed. Rep. of Germany

[21] Appl. No.: 253,516
[22] PCT Filed: Aug. 9, 1980
[86] PCT No.: PCT/DE80/00118
  § 371 Date: Apr. 13, 1981
  § 102(e) Date: Apr. 13, 1981
[87] PCT Pub. No.: WO81/00355
  PCT Pub. Date: Feb. 19, 1981

[30] Foreign Application Priority Data

Aug. 13, 1979 [DE] Fed. Rep. of Germany ....... 2932719

[51] Int. Cl.³ .............................................. A61M 5/00
[52] U.S. Cl. .................................... 604/135; 604/136;
[58] Field of Search ........... 128/218 F, 218 A, 218 R, 128/218 G, 215, 232

[56] References Cited

U.S. PATENT DOCUMENTS

| 3,572,336 | 3/1971 | Hershberg | 128/218 M |
| 4,114,619 | 9/1978 | Wagner | 128/215 |
| 4,284,077 | 8/1981 | Wagner | 128/218 A X |

FOREIGN PATENT DOCUMENTS 2620358 11/1977 Fed. Rep. of Germany ... 128/218 G

Primary Examiner—John D. Yasko
Attorney, Agent, or Firm—Hane, Roberts, Spiecens & Cohen

[57] ABSTRACT

A hypodermic syringe comprising a housing having a needle chamber and a sealed receiving chamber containing an injection liquid. A hollow needle is mounted for slidable displacement in the needle chamber in a retracted position. A first piston acts on the hollow needle for displacing it to an extended position in which the needle projects from the housing for piercing the skin. A second piston in the receiving chamber acts on the injection liquid to pressurize the same. An apparatus holds the first and second pistons in respective retracted position with a passage connecting the first and second chambers and also being provided with a closure normally closing the passage. An actuator releases the holding apparatus to permit the first and second pistons to move to respective extended positions in which the hollow needle is displaced to its extended position and the injection liquid is pressurized whereby the closure is positioned in the path of travel of the hollow needle for being rendered inoperative thereby in its travel to the extended position whereupon the passage establishes communication between the receiving chamber and the hollow needle whereby injection liquid flows from the receiving chamber to the hollow needle under the pressure applied to the injection liquid by the second piston.

11 Claims, 8 Drawing Figures

U.S. Patent  May 24, 1983  Sheet 1 of 2  4,384,579
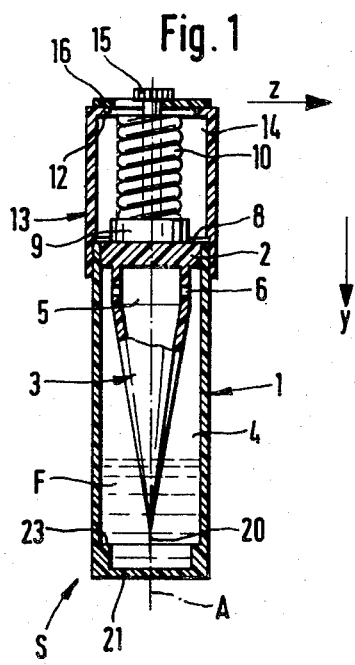
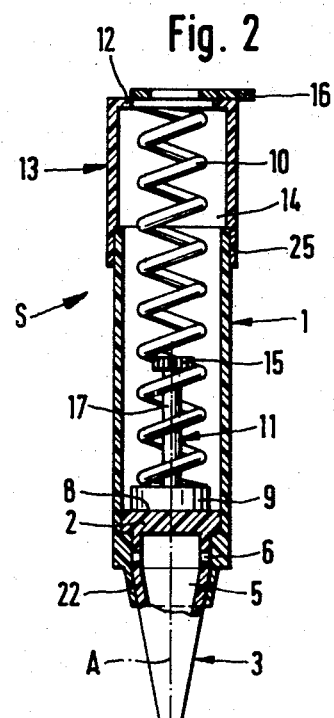
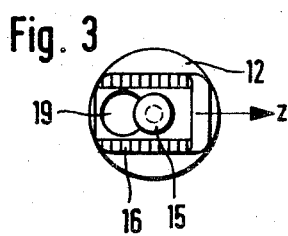
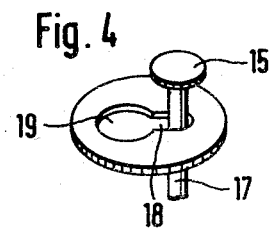
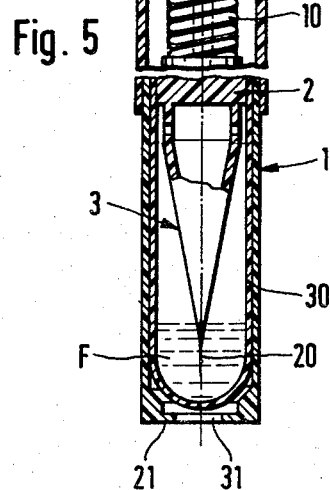

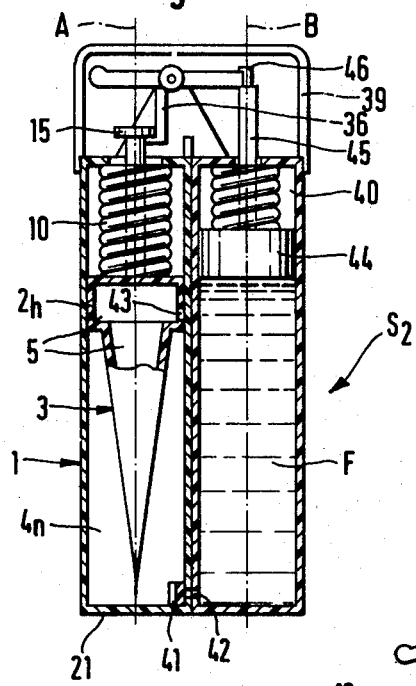
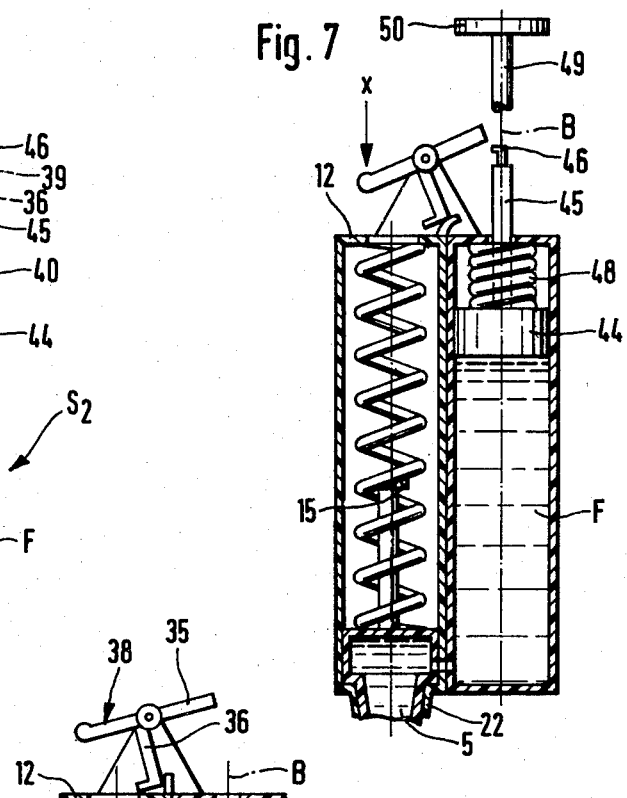
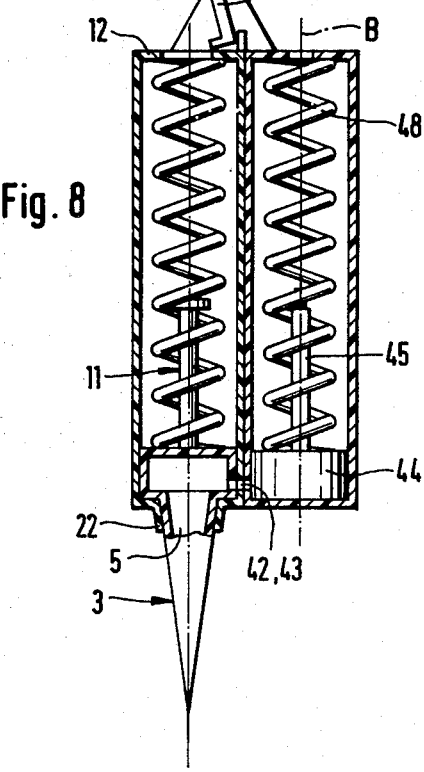

HYPODERMIC SYRINGE

BACKGROUND OF THE INVENTION

The present invention relates to a hypodermic syringe having within its housing a receiving chamber for an injection liquid which can be placed under pressure by a piston or the like and having a hypodermic needle. Disposable syringes of this type are known in which the needle must be screwed onto the syringe in order to make it operable. The injection liquid is taken from ampules and aspirated into the syringe. The handling of such syringes is hygienically unobjectionable and furthermore it is time-consuming.

SUMMARY OF THE INVENTION

It is an object of the invention to provide a hypodermic syringe of the aforementioned type which can be used immediately and satisfies all hygienic requirements. It is another object that the hypodermic syringe be simple to manufacture and so inexpensive that it can be used as a disposable syringe.

In order to achieve this purpose, the hypodermic needle is arranged in a needle chamber which is associated with the reception chamber for the injection liquid and the needle can be displaced by a piston or the like from the needle chamber and can be connected with the receiving chamber in an operating position.

It also resides within the scope of the invention to provide the injection needle with an inner space which widens out conically in the direction opposite the direction of the thrust of the piston and to arrange the needle within the injection liquid; furthermore, the needle is to be developed in such a manner that it can be transferred by the piston from the receiving chamber into an operating position. In this case the needle of the hypodermic syringe of the invention preferably lies within a cylindrical space in which the needle attached to the piston can be displaced by the force of a force accumulator and thereby emerges from the cylinder so as to assume the so-called operating position. The needle therefore comes out of its covering only when it is to be used and cannot be contaminated previously. This is true also in the case of the hypodermic needle which was first mentioned, in which the needle itself is arranged in a space separate from the liquid but completely covered and is filled with liquid only in the operating position.

It has proven particularly favorable to arrange the injection needle in a bag which preferably contains the injection liquid. The tip of the needle perforates this bag when the needle is brought into the operating position and therefore when pressure is exerted on the piston.

The piston which, in accordance with the invention, bears the needle and closes off the top of the liquid chamber is also under the pressure of a force accumulator in the same way as the other piston which is provided merely for the guidance of the needle and adjoining which, in accordance with another feature of the invention, a further piston for the ejection of the liquid is present in a neighboring space. The force accumulators are under tension in the position of rest of the syringe of the invention and are held by locking or closure elements which must be capable of operation in simple manner. For this there has proven to be particularly favorable a locking plate having a keyhole-like cutout which holds a head of a separate push piston. This push piston holds the force accumulator, developed as a coil spring, fast in its force-accumulation position so that this part of the syringe can be removed from the rest of the syringe without the danger of relaxation of the spring. It is also possible to make separate use again of this part of the syringe, which in accordance with the invention is arranged in a protective cap.

In the case of the hypodermic syringe with separate needle and liquid chambers there may also be used, in accordance with the invention, a lever system which on the one hand holds a detent member of the needle piston or the push bolt and on the other hand the piston for the liquid fast, in which case—in accordance with another feature of the invention—the liquid piston is developed so that it can be released from the lever system with time delay for the liberation of the needle piston. As a result of this measure, the hypodermic needle is first engaged in its so-called operating position before it is acted on by liquid, which considerably broadens the field of use of the hypodermic needle of the invention and in particular prevents any problems with the so-called aspiration.

Furthermore, it has proven favorable to develop the cylinder bottom of the reception chamber for the hypodermic needle of a material which can be perforated by the tip of the needle and which preferably also surrounds the needle in the form of a sleeve after the perforation, for instance in the manner of a rubber which lies against the needle.

When the hypodermic syringe is provided with a liquid bag it is sufficient to provide an opening in the bottom of the cylinder, the edges of this opening serving as abutment for the bag upon piercing of the bag by the needle.

If the syringe of the invention has two adjacent receiving chambers for needle and liquid then in accordance with the invention they are connected by an opening in the region of the cylinder bottoms and in the position of rest of the hypodermic syringe are temporarily separated from each other by a closure element, for instance a small sealing plate. The sealing plate is so developed that it is removed or crushed upon the impingement of the needle piston and thus provides a passage for the liquid which can then penetrate into the inside of the needle.

BRIEF DESCRIPTION OF THE DRAWING

Further advantages, features and details of the invention will become evident from the following description of preferred embodiments when read with reference to the drawing, in which:

FIG. 1 is a longitudinal section through a hypodermic syringe, shown in position of rest;

FIG. 2 shows the hypodermic syringe of FIG. 1 in operating position;

FIG. 3 is a top view of FIG. 1;

FIG. 4 is an oblique view of a detail of another embodiment;

FIG. 5 is a longitudinal section through another embodiment of the hypodermic syringe;

FIG. 6 is a longitudinal section through another embodiment, shown in position of rest;

FIG. 7 shows the hypodermic syringe of FIG. 6 in operating position;

FIG. 8 shows the hypodermic syringe of FIGS. 6, 7 in emptied condition.

DETAILED DESCRIPTION OF THE PREFERRED EMBODIMENT

A hypodermic syringe S for liquid medicaments or injection liquids F has, as shown in FIG. 1, a piston 2 within a cylinder 1, a hollow needle 3—shown in exaggerated cross section in the drawing—extending from the piston into the cylinder chamber 4 which receives said injection liquid F. The inside 5 of the needle communicates with the cylinder chamber 4 by perforations 6.

In the longitudinal axis A of the syringe, the head 9 of a slide bolt 11 (FIG. 2) acted on by a spring 1 presses against the surface 8 of the piston remote from the needle. This coil spring 10 rests at the one end against the head 9 and at the other end against the inside of an abutment plate 12 which is part of a cap-like top 13 with cap chamber 14.

Towards the top the push bolt 11 terminates in a bolt head 15 which, in the tensioned position of the coil spring 10 shown—and therefore in the position of rest of the hypodermic syringe S—is seated over a locking plate 16, namely over a slot 18 which is traversed by the shaft 17 of the push bolt (FIG. 4). Adjoining this slot is a cutout 19 which is larger than the cross section of the bolt head 15. The cutout 19 and the slot 18 together form an opening of keyhole shape.

If the locking plate 16 is moved in the direction of the arrow z from its locking position shown in FIG. 3, the coil spring 10 pulls the push bolt 11 in the direction y of extension through the cutout 19 in the locking plate 16 and the tip 20 of the hollow needle 3 penetrates the cylinder bottom 21, the remainder of which rest snugly laterally as sleeves 22 against the hollow needle 3.

The liquid F which fills the cylinder space 4 when the hollow needle 3 is in the position of rest shown in FIG. 1 is pressed by the travel of the piston 2 through the hollow needle 3 until the piston 2 rests against a lower annular shoulder 23; the inside 5 of the needle is then completely closed off.

In the embodiment shown in FIG. 5, the liquid F is arranged in a sack 30 which is fixed partially to the wall 1 of the cylinder or—not shown in the drawing—can be closed via the piston 2. Upon the unlocking of this syringe $S_1$, the tip 20 perforates the bag 30 in the region of a lower opening 31 in the bottom of the cylinder; the bag 30 is held in the cyinder 1 by the cylinder bottom 21 which in this case is of ring shape.

The hypodermic syringe $S_2$ of FIG. 6 consists of two receiving chambers 4,40 with parallel longitudinal axes A, B. The one receiving chamber 4 contains the hollow needle 3, in this case without the injection liquid F, which is arranged in the parallel reception chamber 40.

After the removal of a protective cap 39, the bolt head 15 is released by pressure (arrow x) (FIG. 7) on a lever lock 38 and the piston $2_h$—in this case hollow—is guided by the spring 10 down to the bottom 21 of the cylinder, a lateral seal 41 being thereby destroyed; this seal closes a passage 42 to the adjacent receiving chamber 40 which is connected with the inside 5 of the needle by perforations 43 in the hollow piston $2_h$. The liquid F immediately flows into the inside 5 of the needle under the pressure of a piston 44 which is acted on by a spring 48.

In the position of rest shown in FIG. 6 an axial guide bar 45 of the liquid piston 44 holds a hook 36 by the pressure of a driver 46 against a tilt lever 35 under the bolthead 15—and thus holds the latter in locking or closed position. With a time delay as compared with the lowering of the push bolt 11 the tilt lever 35 detaches itself from the guide rod 45 so that the latter releases the liquid piston 44. The time delay can be produced, for instance, by slotted-link elements, not shown.

The hypodermic syringe S or $S_1$ consists essentially of two parts which can easily be separated from each other, namely the lower syringe part 1 with needle 3 and liquid F and the upper push part with the spring 10 tensioned on the push bolt 11 and the locking device 16. The two parts can be connected with each other in the region 25 by a screw thread and thus be detached from each other.

The hypodermic syringe $S_2$ is of a correspondingly simple construction. In order to permit a slow displacement of the liquid piston 44, the shaft 45 thereof can furthermore be provided with a hand grip 50 which in its turn has a shaft 49.

What is claimed is:

1. A hypodermic syringe comprising a housing having a needle chamber and a receiving chamber, a hollow needle mounted for slidable displacement in said needle chamber in a retracted position, said receiving chamber being sealed and containing an injection liquid therein, first piston means acting on said hollow needle for displacing said needle to an extended position in which the needle projects from said housing for piercing the skin of a subject against which the housing is placed, second piston means in said receiving chamber for acting on said injection liquid to pressurize the same, holder means holding said first and second piston means in respective retracted position, passage means connecting said first and second chambers, closure means normally closing said passage means, and actuator means for releasing said holder means to permit said first and second piston means to move to respective extended positions in which the hollow needle is displaced to its extended position and the injection liquid is pressurized, said closure means being positioned in the path of travel of said hollow needle for being rendered inoperative thereby in its travel to said extended position whereupon said passage means now establishes communication between said receiving chamber and said hollow needle whereby injection liquid flows from said receiving chamber to said hollow needle under the pressure applied to said injection liquid by said second piston means.

2. A syringe as claimed in claim 1 wherein said hollow piston is provided with perforation means which connect with said passage means when said hollow needle is displaced to said extended position whereby said injection liquid can flow from said injection chamber directly into said hollow needle.

3. A syringe as claimed in claim 1 wherein said actuator means and said holder means are cooperatively constructed and engaged such that said first piston means is activated before said second piston means.

4. A syringe as claimed in claim 1 wherein each said piston means comprises a respective associated spring means acting to displace the piston means to extended position.

5. A syringe as claimed in claim 3 wherein said actuator means comprises a pivotal lever having a first portion engaged with said first piston means and a second portion engaged with said second piston means such that pivotal movement of said lever releases said first and second piston means.

6. A syringe as claimed in claim 5 wherein said pivotal lever includes an engaging portion for pivoting said lever.

7. A syringe as claimed in claim 6 wherein said first and second portions of said lever are constructed to first release said first piston means and then release said second piston means.

8. A syringe as claimed in claim 6 comprising a removable cover on said housing enclosing said pivotal lever and said holding means.

9. A syringe as claimed in claim 6 comprising a manually engageable element coupled to said second piston means for manually holding said second piston means in retracted position after release thereof by said holder means thereby permitting manual control of the displacement of said second piston means to its extended position.

10. A syringe as claimed in claim 1 wherein said needle chamber and receiving chamber are disposed in parallel adjacent relation, said first and second piston means being movable along parallel paths.

11. A syringe as claimed in claim 1 wherein said needle chamber has an end wall facing said hollow needle which is constructed for being pierced by said needle as it travels to said extended position, said end wall serving as an abutment for holding said hollow needle in said extended position.

* * * * *